United States Patent [19]
Feingold et al.

[11] Patent Number: 4,919,650
[45] Date of Patent: Apr. 24, 1990

[54] INFUSION PUMP

[75] Inventors: Vladimir Feingold, Cherrybrook; Peter C. Allworth, Wollstonecraft, both of Australia

[73] Assignee: Bionica Pty. Limited, Castle Hill, Australia

[21] Appl. No.: 174,770

[22] Filed: Mar. 29, 1988

[30] Foreign Application Priority Data

Mar. 30, 1987 [AU] Australia .................... PI1140

[51] Int. Cl.[5] .................... A61M 5/00; F04B 49/06
[52] U.S. Cl. .................... 604/67; 417/22; 417/36; 128/DIG. 13; 222/14; 604/155
[58] Field of Search .................... 604/65–67, 604/151, 155, 154; 128/DIG. 13; 222/14, 63; 417/12, 22, 18, 36

[56] References Cited

U.S. PATENT DOCUMENTS 4,498,843  2/1985  Schneider et al. ............. 604/67 X
4,767,406  8/1988  Wadham et al. ............... 604/155
4,769,009  9/1988  Dykstra ......................... 604/155

Primary Examiner—Stephen C. Pellegrino
Attorney, Agent, or Firm—Ladas & Parry

[57] ABSTRACT

A portable infusion pump assembly utilizing continuous drive propulsion means (8) to effect automatic and incremental displacement of a plunger (5) within a disposable syringe (3) so as to deliver accurately repeatable volumes of fluid from the syringe (3) over a predetermined period of time.

Intermittent drive of the continuous drive propulsion means (8) is effected. Comparison of desired delivery rate with actual delivery rate is made by use of angular displacement signals received from a shaft encoder (10) attached to the shaft of the continuous propulsion means (8).

This method of control also allows indirect measurement of fluid pressure in the syringe (3) without the need for a pressure sensor to be located in direct contact with the fluid being delivered.

25 Claims, 16 Drawing Sheets

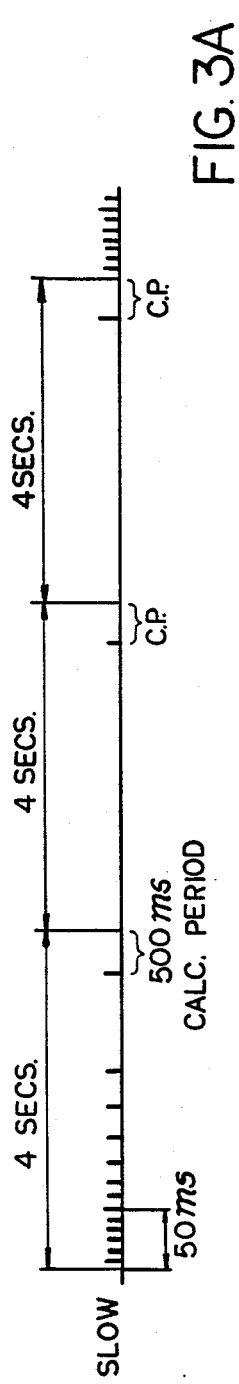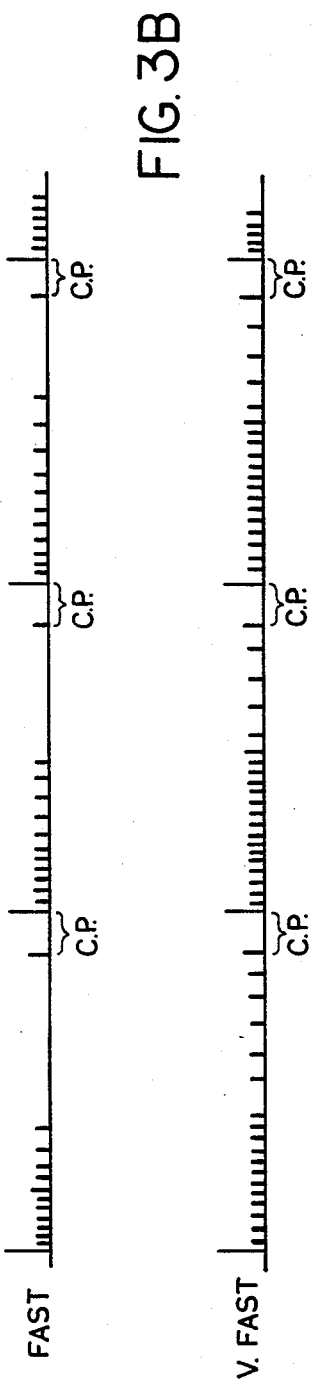
FIG. 3A
FIG. 3B
FIG. 3C

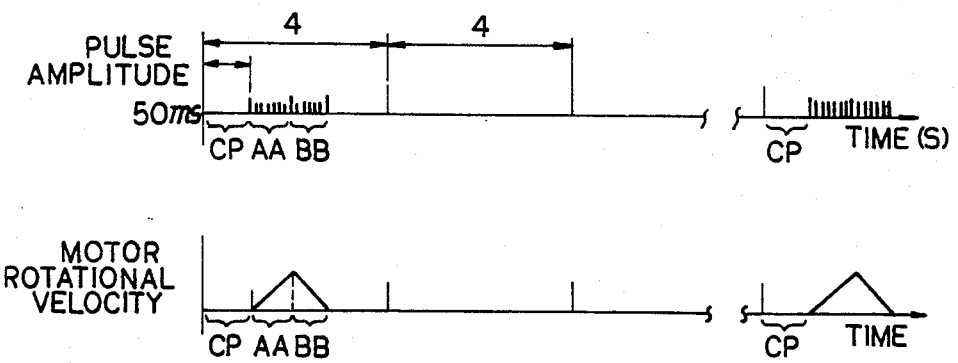
FIG. 5A (SLOW FEED, NORMAL LOAD)
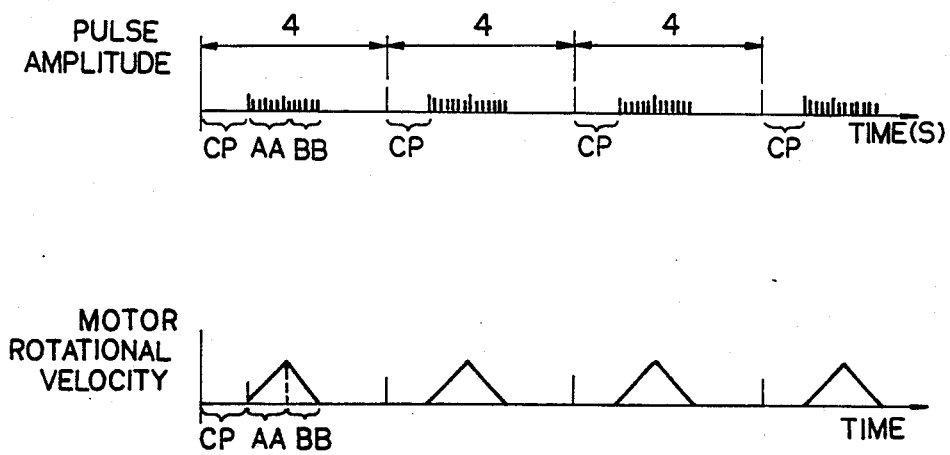
FIG. 5B (FAST FEED, NORMAL LOAD)

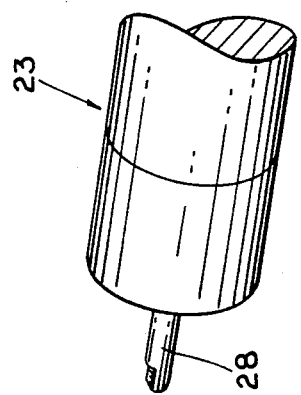
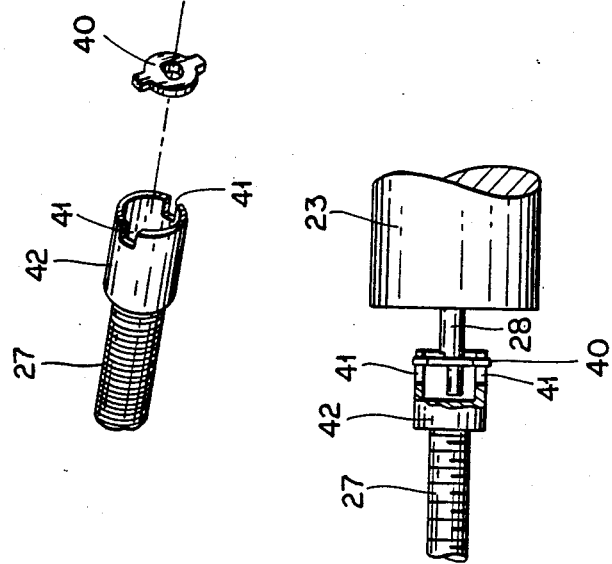
FIG. 9A
FIG. 9B

INFUSION PUMP

TECHNICAL FIELD

The present invention relates to an infusion pump and, in particular, an infusion pump which utilizes a continuous drive propulsion means.

BACKGROUND ART

Prior art infusion pumps and, in particular, those used for medical purposes for infusing relatively small quantities of liquid over a predetermined period of time into a patient's body have typically used stepper motors to drive the pumping mechanism. The main reasons for this appears to relate to the requirement in many infusion situations that the proportion of material delivered per unit of time must be closely regulated. A stepper motor allows regulated metering without the necessity for using feedback circuits. Stepper motors are, however, relatively expensive propulsion devices and can be somewhat inflexible where a wide range of accurately proportioned delivery rates is required in the one infusion device. They are also inefficient and have lower torque output.

Given the preferred use of disposable components in drug delivery systems it is desirable to provide an infusion system which does not contain any invasive components in direct contact with the fluid to be delivered. This might be required if pressure feedback was desired in combination with a stepper motor drive.

It is an object of the present invention to overcome or substantially ameliorate the abovementioned disadvantages whilst utilizing a continuous drive type motive means for the infusion pump.

SUMMARY OF INVENTION

According to one aspect to the present invention there is provided a method of controlling an infusion pump, said pump including a DC motor connected by its output shaft to a reduction gearbox and thence to a rotary to linear motion converter, said converter imparting linear thrust to a syringe piston; said shaft of said DC motor also driving encoding means, said encoding means providing output pulses in proportion to angular displacement of said shaft; said method comprising:

providing power to said DC motor only for a first period of time within a time window during which a first series of output pulses is produced from said encoding means;

monitoring said output pulses (as said shaft of said DC motor returns to a stationary state) during a second period of time during said time window;

comparing said pulses with a desired number of pulses corresponding to a predetermined volume feed rate and, on the basis of said comparison determining whether and for how long to energize said DC motor during subsequent window periods.

In a further broad from there is provided a method of controlling an infusion pump, said pump including a motor adapted to impart continuous rotary motion via an output shaft, said pump further including encoding means adapted to provide data indicative of rotational motion of said output shaft, said data being proportional to the angular displacement of said output shaft; said method comprising providing power to said motor only for a first period of time within a time window during which first data is produced from said encoding means; monitoring second data received from said encoding means during a second period of time immediately following said first period of time during said time window; comparing said first and second data with desired data corresponding to a predetermined volume feed rate of said infusion pump and, on the basis of said comparison, determining whether and for how long to energize said motor during subsequent window periods.

Preferably said encoding means comprises a pulse encoder which produces output pulses proportional to angular displacement of said output shaft.

Preferably said first data comprises pulses received from said encoder, the number of said pulses being proportional to the angular displacement of said output shaft during said first period of time during which and only during which power is provided to said motor.

Preferably said second data comprises output pulses received from said encoding means during said second period of time, said second period of time being the time taken for said output shaft to come to standstill following removal of power from said motor.

Preferably said motor is a DC motor.

Preferably said window period lies in the range of 1-5 seconds.

Preferably if said comparison indicates that less than a predetermined minimum amount of displacement of said output shaft is required for a subsequent window period then said motor is not energized during said subsequent window period.

In yet a further broad form there is provided an infusion pump including a motor adapted to impart continuous rotary motion via an output shaft, said pump further including encoding means adapted to provide data indicative of rotational motion of said output shaft, said data being proportional to the angular displacement of said output shaft; said pump further including means to provide power to said motor only for a first period of time within a time window during which first data is produced from said encoding means; comparison means for comparing said first data and second data received from said encoding means during a second period of time immediately following said first period of time during said time window with desired data corresponding to a predetermined volume feed rate of said infusion pump; said comparison means determining whether and for how long to energize said motor during subsequent window periods on the basis of the comparison.

Preferably said encoding means comprises a pulse encoder which produces output pulses proportional to angular displacement of said output shaft.

Preferably said first data comprises pulses received from said encoder, the number of said pulses being proportional to the angular displacement of said output shaft during said first period of time during which, and only during which, power is provided to said motor.

Preferably said second data comprises output pulses received from said encoding means during said second period of time, said second period of time being the time taken for said output shaft to come to a standstill following removal of power from said motor.

Preferably said motor is a DC motor.

Preferably said time window lies in the range 1-5 seconds.

In yet a further broad form there is provided an infusion pump, said pump including a DC motor connected by its output shaft to a reduction gearbox and thence to a rotary to linear motion converter, said converter imparting linear thrust to a syringe piston; said shaft to said DC motor also driving encoding means, said encoding means providing output pulses in proportion to angular displacement of said shaft; said pump including control means to supply power to said DC motor only for a first period of time within a time window during which a first series of output pulses is produced from said encoding means; said control means monitoring said output pulses (as said shaft of said DC motor returns to a stationary state) during a second period of time during said time window; said control means comparing said pulses received drug said first and said second periods and comparing said pulses with a desired number of pulses corresponding to a predetermined volume feed rate and, on the basis of said comparison, determining whether and for how long to energize said DC motor during subsequent window periods.

Preferably the acceleration of said output shaft is approximately constant during said first period of time and deceleration of said output shaft is approximately constant during said second period of time.

Preferably said first period of time and said second period of time are approximately equal.

In a preferred form the total length of said first period of time and said second period of time does not exceed 1 second.

In a particular preferred form said time window is approximately 4 seconds, said reduction gearbox has a reduction ratio of approximately 700:1, said syringe piston has an inside diameter of approximately 15 mm plus/minus 0.5 mm and said delivery rate does not exceed 5 ml/hr. Alternatively said time window is set at approximately 2 seconds, causing the maximum delivery rate to be approximately 10 ml/hr.

BRIEF DESCRIPTION OF THE DRAWINGS

The present invention will now be described with reference to preferred embodiments wherein:

FIGS. 3A, 3B and 3C are indicative timing diagrams of pulse trains associated with the feedback means of the first embodiment;

FIGS. 5A and 5B are timing and velocity/time diagram for the second embodiment;

FIGS. 9A and 9B are exploded perspective and, partly in section, detailed side views, respectively, of a flexible coupling suitable for use with either the first or second embodiments.

MODES OF CARRYING OUT THE INVENTION

The circuit and rationale behind the preferred embodiments below described relates to providing an inexpensively constructed infusion pump drive mechanism utilizing a continuous drive type motor together with appropriate feedback means which will provide accurate delivery, or at least repeatable delivery, of predetermined amounts of liquid over preselected periods of time ranging from minutes to hours or, even, days. Furthermore, all preferred embodiments provide an inherent measure of pressure feedback which does not require the placement of a pressure sensing device in direct contact with the fluid being delivered to the patient. In fact the pressure feedback is inherent in the control method of the preferred embodiments when used in association with a continuous drive type motor.

FIRST PREFERRED EMBODIMENT

Figure 1:
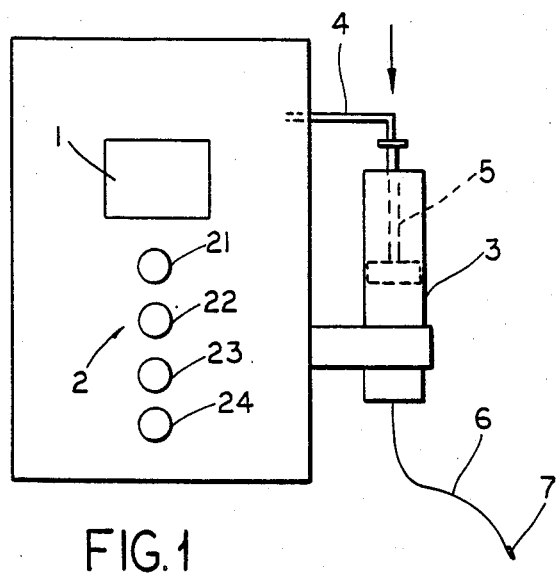
FIG. 1 is an external view of an infusion pump utilizing the motive means according to both the first and second embodiments of the present invention.

Referring to FIG. 1 there is shown an infusion pump assembly comprising a display 1 (digital readout for example), keyboard 2 and syringe 3. The device drives syringe piston 5 by means of an internal mechanism acting upon syringe actuator 4 so as to deliver liquid within the syringe 3 along delivery tube 6 to catheter/needle 7. Typical delivery rates for such devices in medical applications are of the order of microliters per hour.

Figure 2:
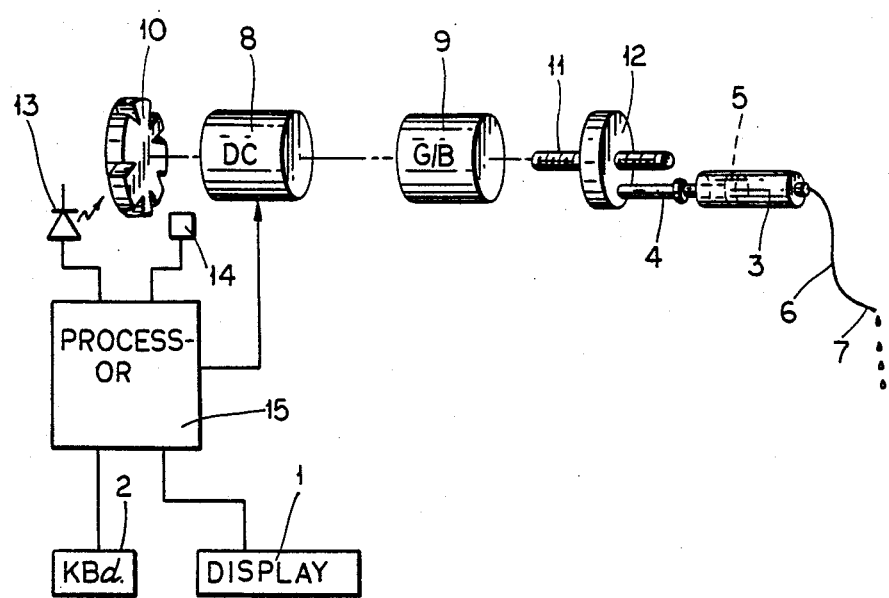
FIG. 2 is a block diagram of the components of the first and second preferred embodiments.

Referring to FIG. 2, some of the internal components of the infusion pump are shown. The syringe drive mechanism comprises a continuous drive type motor, in this case, a DC motor 8 driving a gearbox 9 which rotates a screwdrive 11. The rotating motion of the screw operator 11 is converted to linear motion by the nut 12 which acts upon the syringe actuator 4. Also connected to the shaft of the DC motor 8 is an optical shaft wheel encoder which provides an output pulse train via photo transistor 14 to processor 15. Light emitting diode 13 provides the light source for the photo transistor 14 in the encoder 10. The number of pulses delivered by photo transistor 14 to processor 15 is directly proportional to the angular displacement of the DC motor drive shaft and hence of the linear displacement of syringe piston 5.

Referring to FIG. 3, the behaviour of the pulse train delivered from the encoder is shown for three different delivery speed categories; namely slow, fast and very fast.

Referring to the slow speed mode of FIG. 3(a), the processor 15 delivers power to the DC motor 8 for approximately 50 ms during a 4 second operational "window". During this initial 50 ms period the motor shaft will accelerate and a relatively rapid pulse train will be output from the encoder 10. During a subsequent approximately 200 ms period after power to the motor is cut off the motor shaft will run down to zero speed and this is reflected by a pulse train from the encoder 10 wherein the pulses become progressively more spaced out in time.

Any pulses generated by the encoder 10 during a 4 second "window" are recorded by processor 15 as representative of the delivery volume of fluid during that window ie pulse count is proportional to total volume of fluid delivered.

The processor 15 compares the total volume of fluid delivered including that portion delivered during the 200 ms run on period) as represented by the cumulative pulse count over all window periods with the volume that should have been delivered up to the end of that 4 second window if the delivery rate as set by the user is to be maintained.

On the basis of:
total volume delivered to end of current 4 second window; and
run on characteristic
the controller determines whether to deliver power to the DC motor during the next 4 second window, and, if so, for how long.

Under slow feed conditions the processor will typically only energize the motor once every five and six window periods. Under fast feed conditions the motor is energized during each window period. (Refer faster feed characteristic in FIG. 3(b).)

Under very fast feed conditions the motor will be energized for substantially longer than 50 ms during each window and the run on period will run almost to the end of the window (FIG. 3(c)). In the present embodiment a 500 ms calculation period (CP) is reserved at the end of each 4 second window during which run on pulses are not evaluated. The limit of operation for this embodiment therefore occurs when the motor power time plus the run on time equals the window period (4 seconds) less the calculation period (500 ms). If a faster delivery speed is required it will be necessary to change the gearbox ratio or alter the length of the window period.

In the preferred embodiment of FIG. 2, the gearbox ratio is approximately 700/1 which, together with the 4 second window period allows accurately repeatable delivery rates up to approximately 1 ml per hour.

The pulses generated during the run on period can also be used to determine the pressure of the liquid in the syringe 3. As the torque is increased on the motor due to pressure the number of pulses will reduce. The reduction in the number of pulses is a function of the load torque. Thus the microprocessor can assess these variations and determine the pressure. In extreme cases the behaviour of these pulses can also be used to determine whether the syringe is empty or, alternatively, has jammed.

Figure 4A:
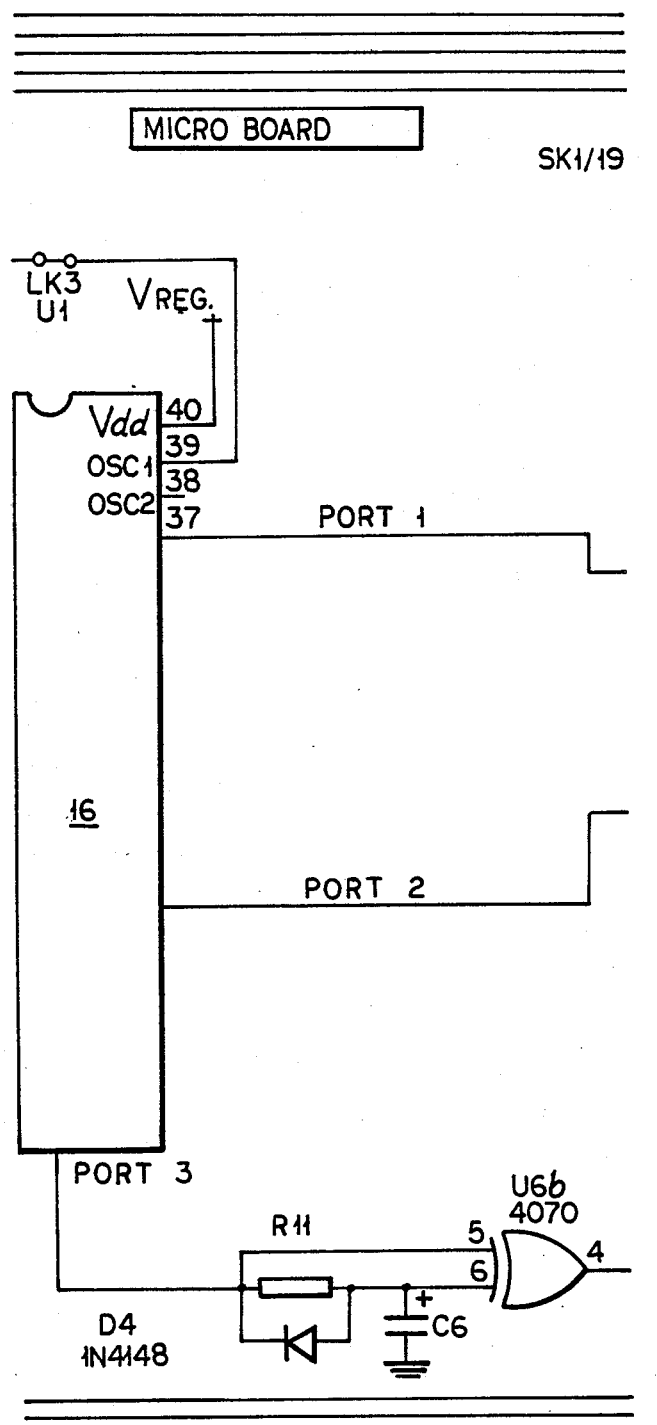
FIGS. 4A and 4B are a schematic diagram of a circuit of the first embodiment of the present invention.
Figure 4B:
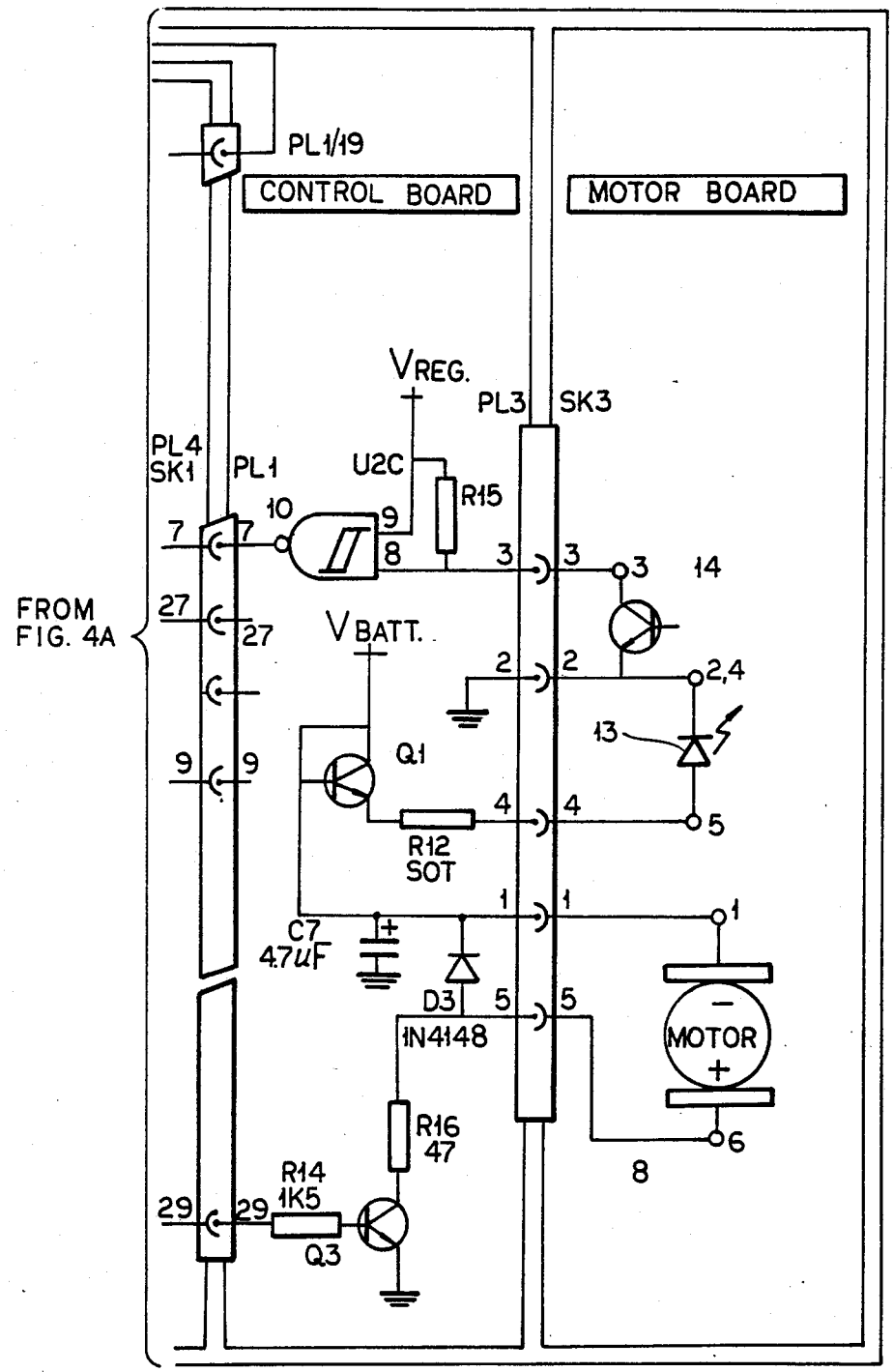
Figure 6A:
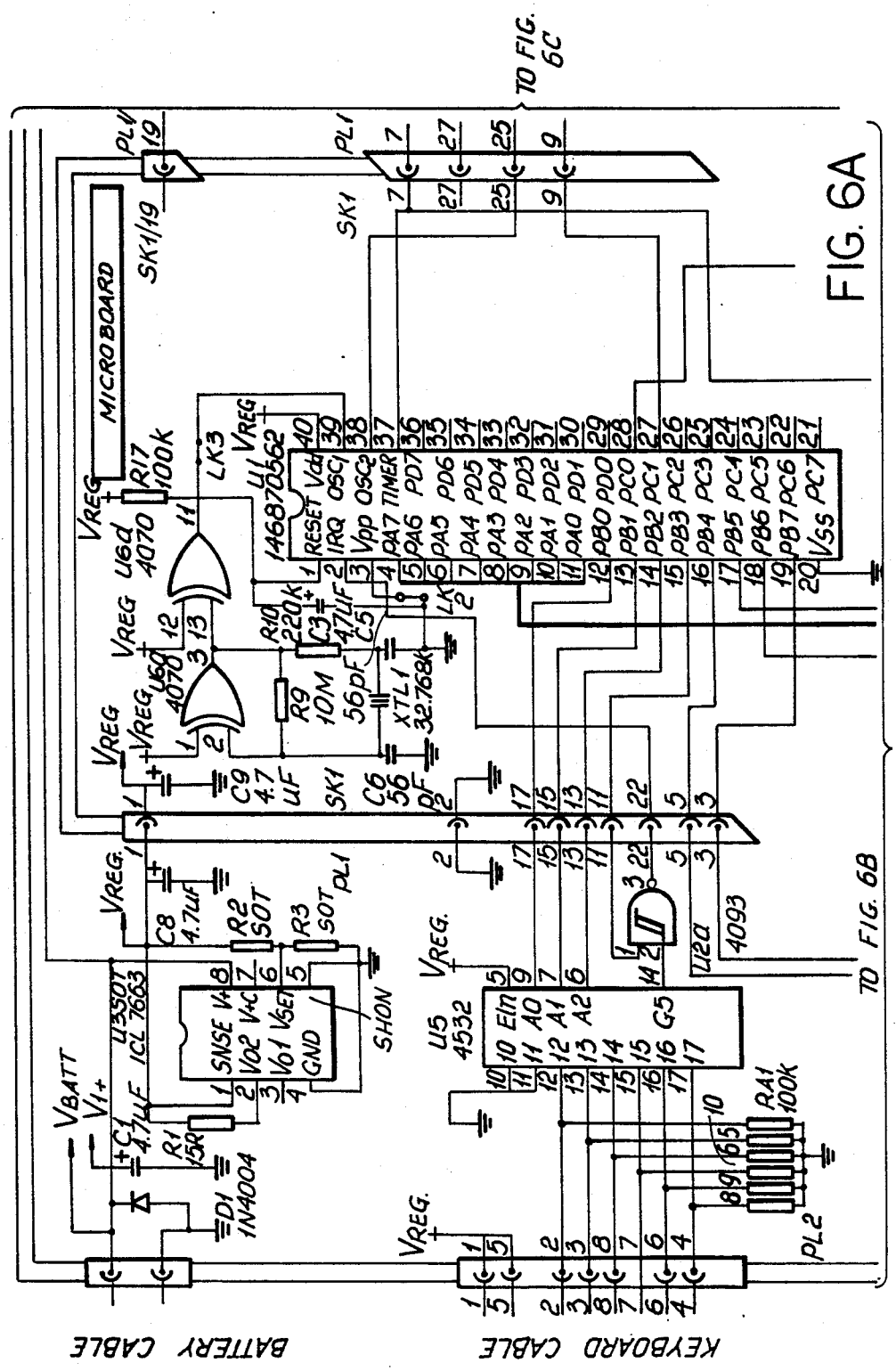
FIGS. 6A, 6B, 6C, 6D and 6E are a schematic diagram of a circuit of the second embodiment of the invention.
Figure 6B:
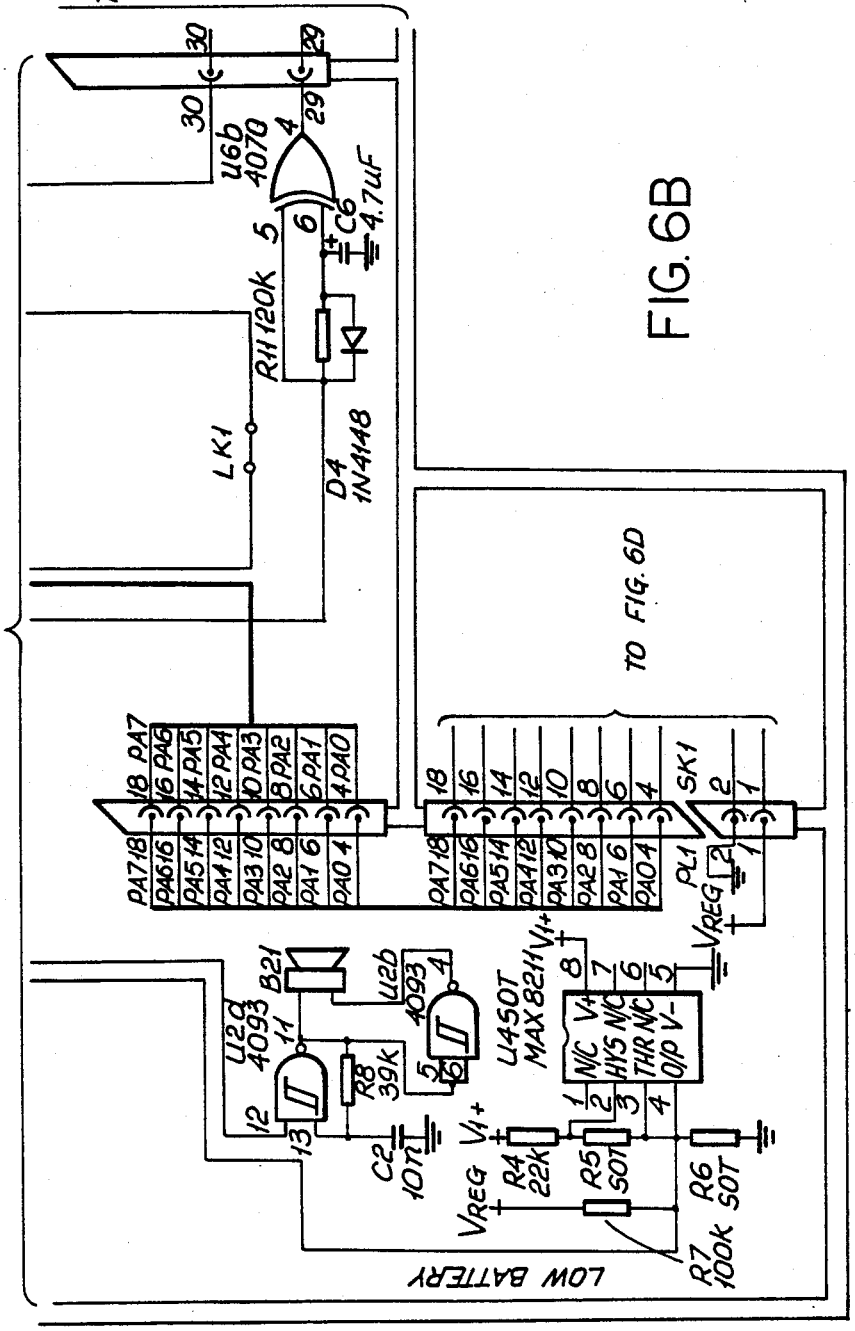
Figure 6C:
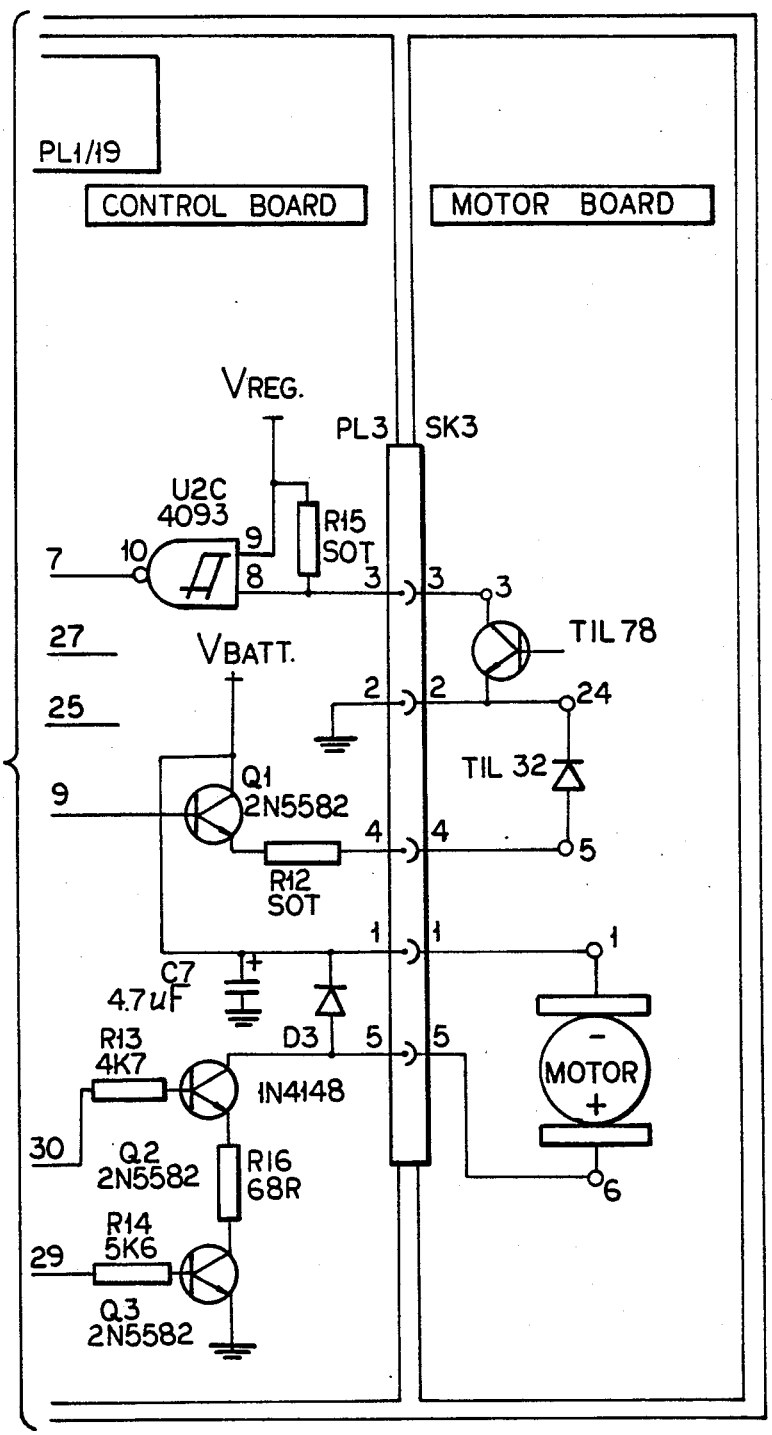
Figure 6D:
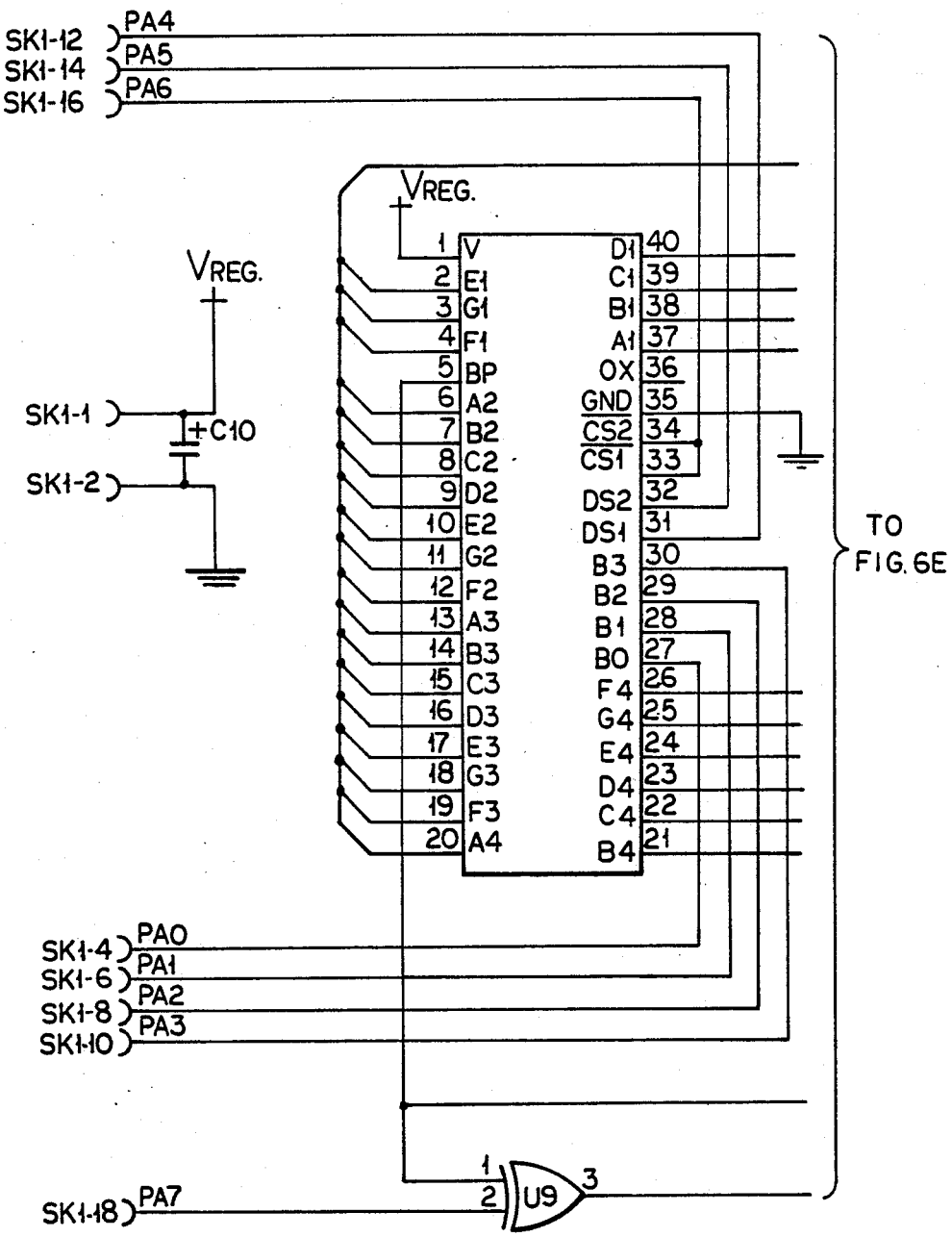
Figure 6E:
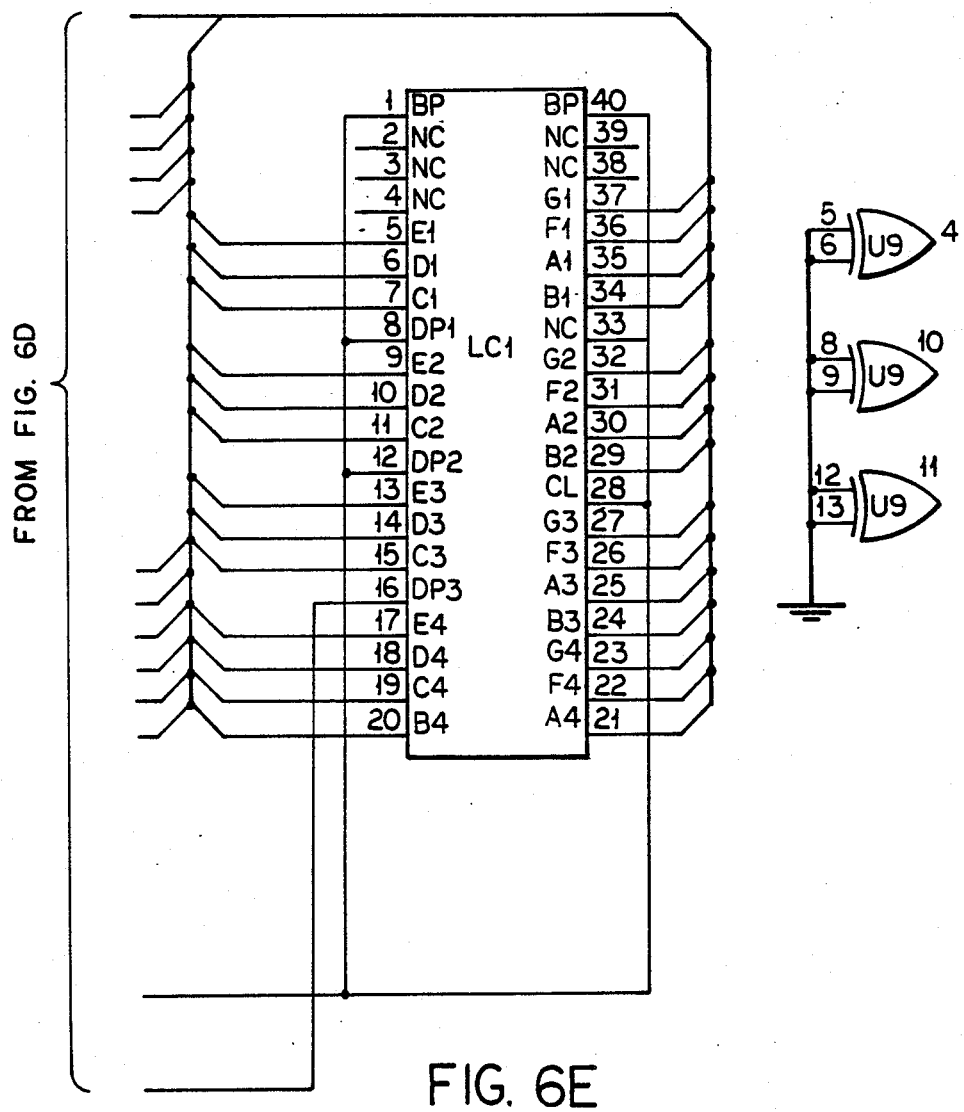

FIG. 4 discloses a motor drive circuit suitable for implementing the control scheme of the first preferred embodiment. Light pulses are received on photo transistor 14 through the opto-encoder from light emitting diode 13 and delivered via a Schmidt trigger circuit to an input port of microprocessor 16. Output ports of the microprocessor 16 drive the DC motor on the basis of the programmed delivery rate in the software within the microprocessor.

An enabling gate ensures that the motor drive cannot remain on beyond a predetermined period of time. This is a safety mechanism ensuring that the control system only drives the motor in a pulsed mode as generally intended. This prevents runaway situations if the microprocessor becomes faulty and attempts to leave the control line continuously at "on" level.

SECOND PREFERRED EMBODIMENT

The second embodiment operates in generally the same fashion as the fist embodiment. The mechanical layouts and drive train of FIGS. 1 and 2 are retained in this second embodiment.

The behaviour of the motor drive during operation is generally as shown in FIG. 5. In this embodiment the calculation period is considered to commence at the beginning of a "window" period and is approximately 50 ms in duration. FIG. 5(a) shows the pulse output behaviour of the encoder 10 as well as a velocity/time characteristics of the drive train for a slow delivery rate under normal load conditions. FIG. 5(b) provides similar data for a fast delivery rate under normal load conditions. FIG. 6 shows the circuit board interconnections and components for the electronics of the second embodiment. FIG. 6 has been divided up into FIG. 6(a) comprising the microprocessor board portion of the circuit, FIG. 6(b) comprising the power electronics control board and power electronics motor board and FIG. 6(c) comprising the electronics for the display of the device of the second embodiment. The component types and interconnections are as shown in FIG. 6.

Figure 7A:
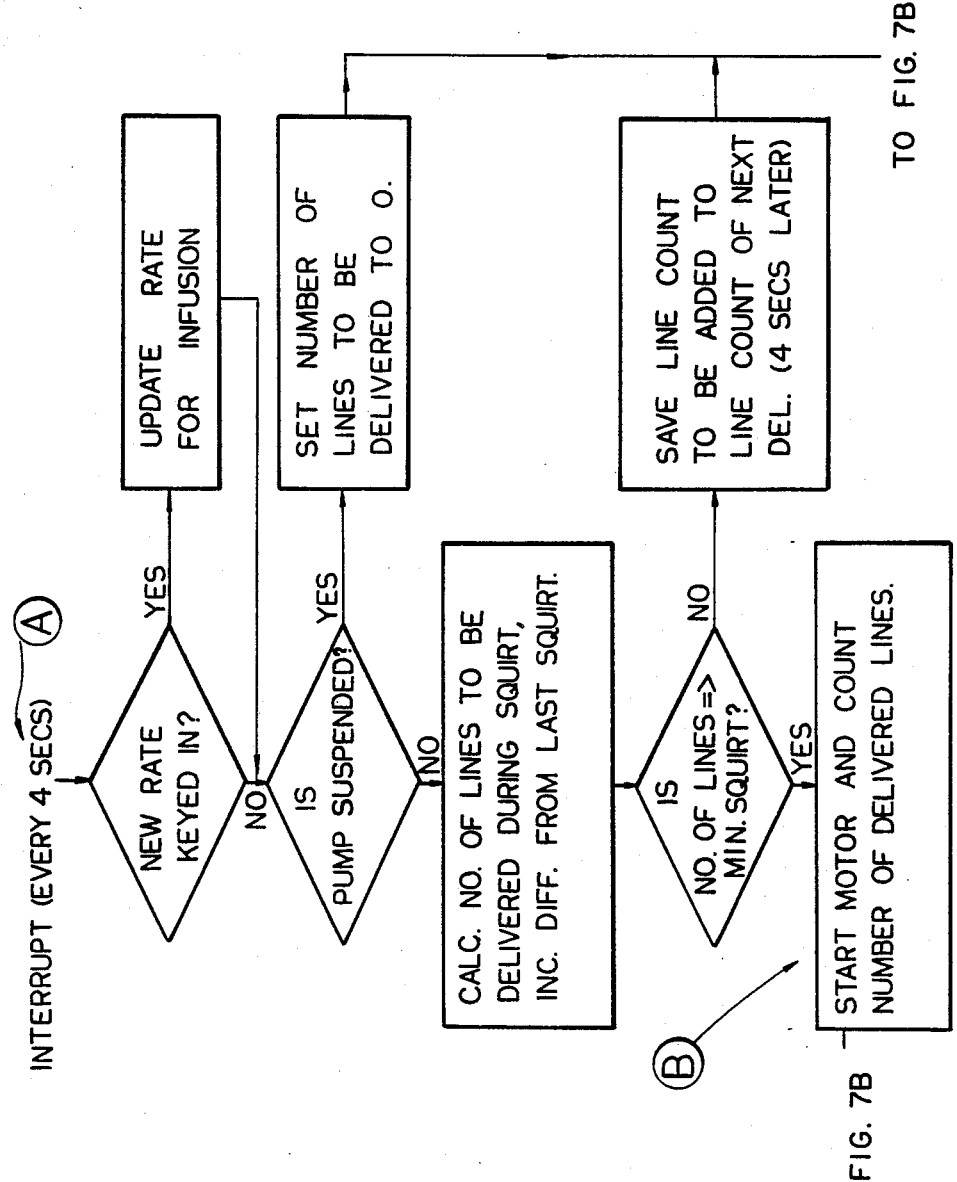
FIGS. 7A, 7B and 7C are a flow chart for the primary control algorithm to be programmed into the microprocessor of the second embodiment.
Figure 7B:
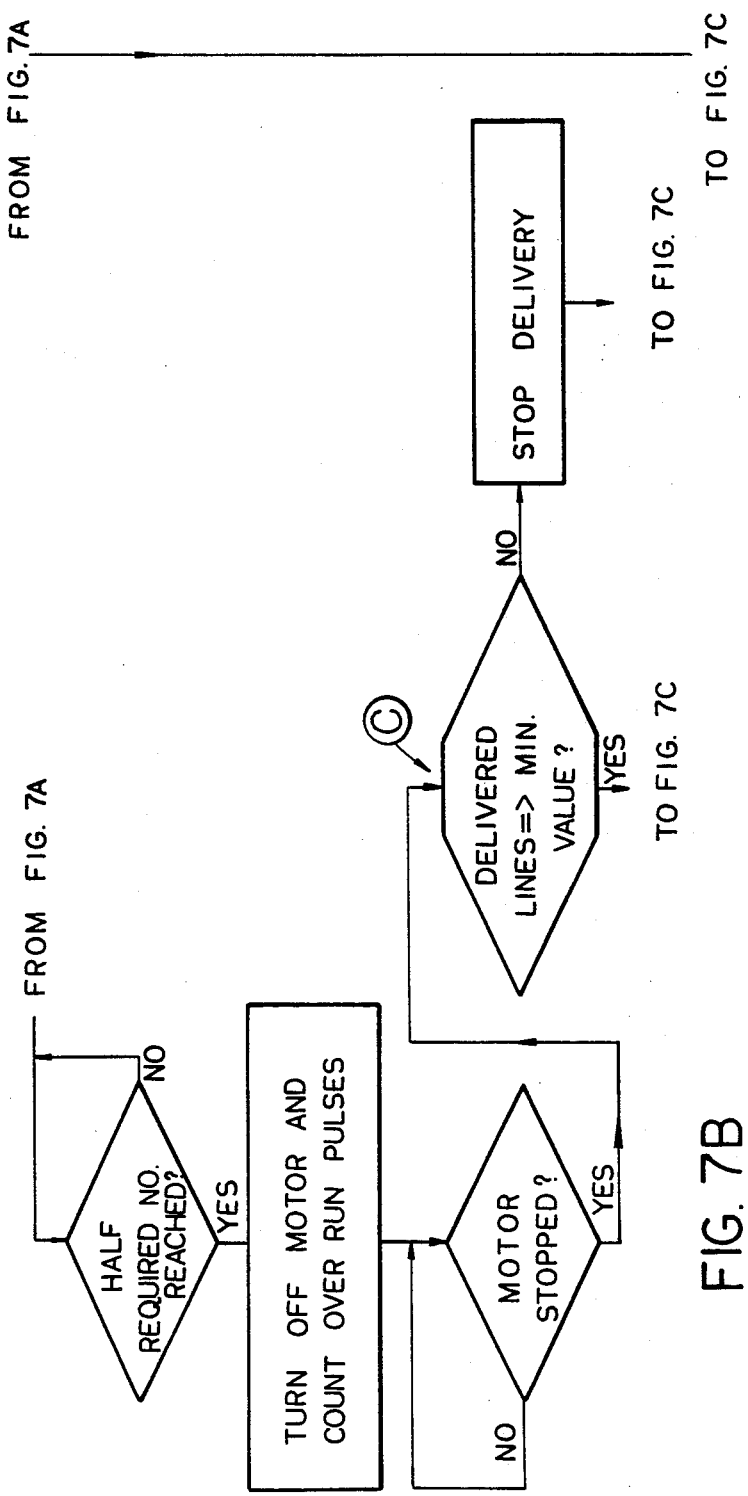
Figure 7C:
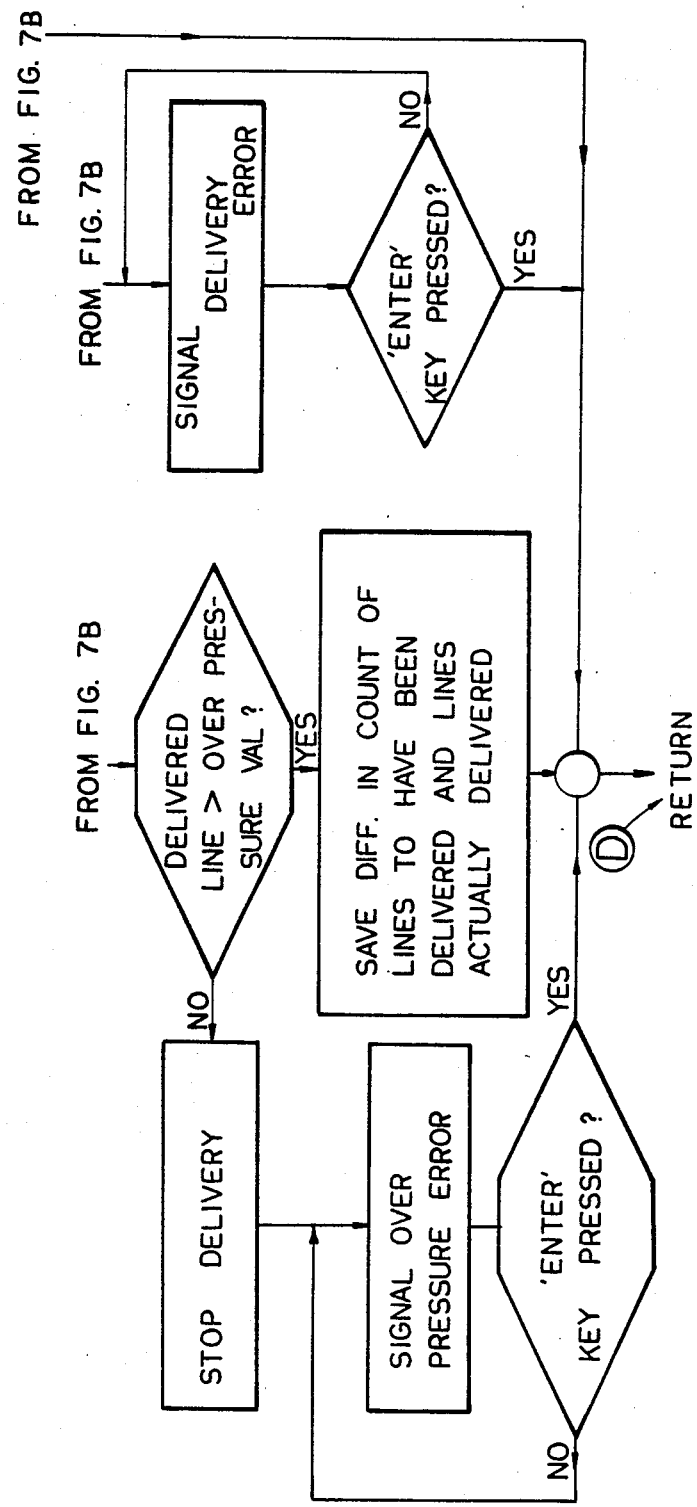

FIG. 7 shows the software logic flow for the second embodiment as programmed into the microprocessor of FIG. 6.

The task of FIG. 7 is initiated by an interrupt to the microprocessor at point A. At this point the calculation period (CP) commences. At point B on the flow chart the calculation period (CP) has essentially terminated with a decision having been made on the basis of stored information and pulse count information as to whether to start the motor or not during this "window" period. As point C the "motor on" period (AA of FIG. 5) and the "motor off—run down period" (BB of FIG. 5) have just finished. At point D of the flow chart of FIG. 7 checks have been made to determine whether there appears to be too much pressure in the fluid delivery chamber of the syringe 3 and/or whether there has been a "delivery error" (less than expected minimum number of pulse counts received during the window period).

In use the operator of the second embodiment (and, indeed, the first embodiment) applies a filled syringe to the drive assembly as generally shown in FIG. 1. The assembly can be primed by placing the unit in "prime" mode by use of mode push button 2.2 and the enter button 2.1. In this mode, by continuously holding the "enter" button 2.1 on the drive assembly will continuously operate so as to ensure that there is fluid along the complete length of the supply line and catheter 6, 7. "Feed rate enter" mode is then selected by use of the mode push button 2.2 and the enter push button 2.1. A specific feed rate is then selected by use of the increase or decrease push buttons 2.3, 2.4. The unit is then placed in "locked" mode whereby the first "calculation period" is initiated. The needle 7 is connected appropriately to the patient or other volume or body to which the fluid is to be delivered. The delivery rate is shown in the display 1 and this rate will be delivered continuously whilst the unit remains in operational mode and no error condition is detected.

Referring to FIGS. 5, 6 and 7, detailed operation is as follows:

Motor operation and pulse monitoring is microprocessor controlled. The microprocessor 16 generates a second operating cycle upon which drug delivery calculations are based. Using data held in permanent memory and data entered via the keypad, the number of pulses to be delivered each 4 seconds, to maintain the rate set by the user, is calculated. This calculation is carried out immediately following each 4 second processor interrupt and is termed the calculation period (CP in the Figures). Experimentation has shown that for small motor operating periods and normal load conditions, motor acceleration and deceleration are approximately equivalent and constant. The processor therefore delivers power to the motor and counts the incoming pulses until half the required total for the "window" period has been received. The processor then cuts power to the motor and continues to count the incoming pulses until the time between pulses is great enough for the processor to conclude that the motor has stopped.

The pulse count is recorded by the microprocessor as representing the volume of fluid ie pulse count is proportional to total volume of fluid delivered.

The processor compares the total volume of fluid delivered (including the portion delivered during the motor run on period) with the volume that should have been delivered during the "window" period. The difference is recorded in memory as an error term is added to the pulses to be delivered at the start of the next 4 second "window" period.

In order to maximise the efficiency of the system, a minimum number of pulses to be delivered per event is incorporated in the software. The processor will not activate the motor until this number is reached. Thus under slow feed conditions, as only a small number of pulses will be required each 4 seconds to maintain the delivery rate set by the user, the motor will typically only be energized once every five or six 4 second intervals. Under fast feed conditions, the motor is energized durng each interval.

Under very fast feed conditions, as the motor is energized for a longer period, acceleration toward the end of the motor on period is no longer constant. The limit of operation for this embodiment therefore occurs when the motor approaches a terminal velocity. If faster delivery rates are required it will be necessary to incorporate a more complex control algorithm, change the gearbox ratio, or reduce the window period to less than 4 seconds.

In the second preferred embodiment, a gearbox ratio of 700:1, a screw operator pitch of 0.5 mm and the 4 second operating cycle will allow accurately repeatable delivery rates from approximately 5 ul/hr up to approximately 5 ml/hour when used in conjunction with commercially available 10 ml syringes (of approximately 15 mm diameter).

Delivery rates in the range 10 ul/hr up to 10 ml/hr can be achieved by reducing the window period to 2 seconds (and otherwise leaving all parameters the same) Other ranges can be accommodated by suitable variation of one or more of these parameters. For very large delivery rates it can be most appropriate to use a larger diameter syringe.

The pulses generated using the run-on period can be used to determine pressure conditions of the liquid in the syringe. Under no load and light load conditions deceleration of the motor is less than acceleration thus the number of motor run-on pulses is high. This will simply mean that the processor will not activate the motor again until enough pulses have been accumulated to compensate for the large error term as well as meet the minimum pulse number criteria.

Similarly, as torque is increased on the motor due to pressure, deceleration will be greater than acceleration and the number of pulses received during the motor run-on period will reduce. The reduction will be a function of the load torque. The microprocessor can assess these variations and determine abnormal pressure conditions. In extreme cases the behaviour of the pulses can also be used to determine whether the syringe is empty or, alternatively, has jammed.

The following Tables 1, 2 and 3 provide specific examples of calculations carried out by the microprocessor over 10 window periods for the cases of "normal load", "no load" and "heavy load" respectively and exemplify the algorithm used in the preferred embodiment flowchart of FIG. 7.

Typical Delivery Data

TABLE 1:

10 ml Terumo Syringe 15.5 mm diameter delivering at 995 ul/hr (minimum delivery=200 pulses)

TABLE 1

| | 10 ml Terumo Syringe 15.5 mm diameter delivering at 995 ul/hr (minimum delivery = 200 pulses) | | | |
|---|---|---|---|---|
| | NORMAL LOAD DELIVERY DATA: | | | |
| WIN-DOW | PULSES RE-QUIRED | MOTOR ON PULSES | RUN-ON PULSES | TOTAL | ERROR |
| 1 | 136 | — | — | — | +136 |
| 2 | 272 | 136 | 160 | 296 | −24 |
| 3 | 112 | — | — | — | +112 |
| 4 | 248 | 124 | 142 | 266 | −18 |
| 5 | 118 | — | — | — | +118 |
| 6 | 254 | 127 | 135 | 262 | −8 |
| 7 | 128 | — | — | — | +128 |
| 8 | 264 | 132 | 143 | 275 | −11 |
| 9 | 125 | — | — | — | +125 |
| 10 | 261 | 130 | 136 | 266 | −5 |

TABLE 2

| | NO LOAD DELIVERY DATA: | | | |
|---|---|---|---|---|
| WIN-DOW | PULSES RE-QUIRED | MOTOR ON PULSES | RUN-ON PULSES | TOTAL | ERROR |
| 1 | 136 | — | — | — | +136 |
| 2 | 272 | 136 | 781 | 917 | −645 |
| 3 | − 509 | — | — | — | −509 |
| 4 | − 373 | — | — | — | −373 |
| 5 | − 237 | — | — | — | −237 |
| 6 | − 101 | — | — | — | −101 |
| 7 | 35 | — | — | — | +35 |
| 8 | 171 | — | — | — | +171 |
| 9 | 307 | 153 | 788 | 941 | −634 |
| 10 | − 498 | — | — | — | −498 |

TABLE 3

| | HEAVY LOAD DELIVERY DATA: | | | |
|---|---|---|---|---|
| WIN-DOW | PULSES RE-QUIRED | MOTOR ON PULSES | RUN-ON PULSES | TOTAL | ERROR |
| 1 | 136 | — | — | — | +136 |
| 2 | 272 | 136 | 71 | 207 | +65 |
| 3 | 201 | 100 | 52 | 152 | +49 |
| 4 | 185 | — | — | — | +185 |
| 5 | 321 | 160 | 90 | 250 | +71 |
| 6 | 207 | 103 | 51 | 154 | +53 |
| 7 | 189 | — | — | — | +189 |
| 8 | 325 | 162 | 84 | 246 | +79 |
| 9 | 215 | 107 | 58 | 165 | +50 |
| 10 | 186 | — | — | — | +186 |

Figure 8:
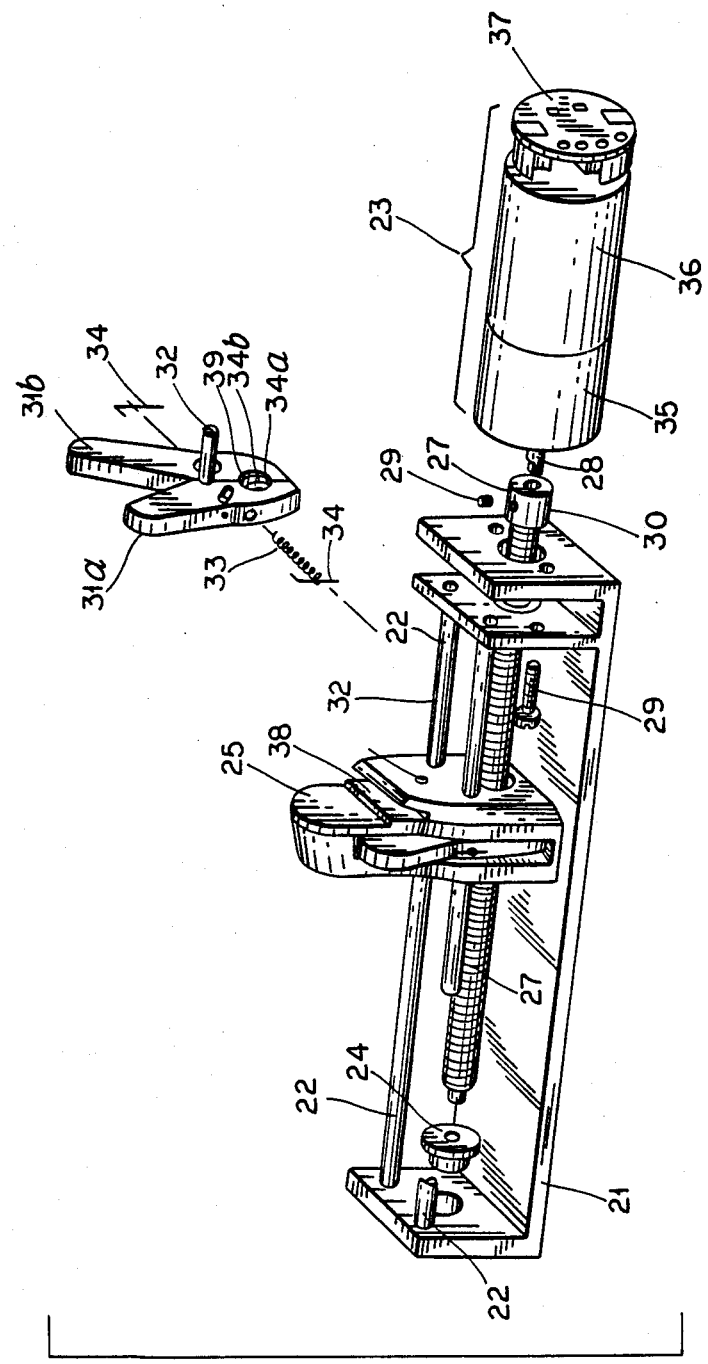
FIG. 8 is an exploded mechanical view of the drive componentry of the second embodiment.

Referring to FIG. 8 the mechanical details of the syringe drive of the second preferred embodiment are shown. The syringe drive mechanism comprises a frame 21, support rails 22, motor assembly 23, screw operator 27, syringe plunger driver 25 and ballbearing 24.

The motor assembly 23 is clamped to the frame by screws 29. The screw operator 27 is supported at one end by bearing 24 located at one end of the frame 21. The screw operator 27 is supported at its other end by the motor shaft 28. The rotary motion of the motor shaft 28 is transmitted to the screw operator 27 by means of a screw 29 which clamps a boss 30 to the motor output shaft 28.

Located within a housing in the syringe plunger drive 25 is a pair of half nuts 31a, 31b supported symmetrically on a pivot pin 32. The nuts are held together on the pin 32 by means of spring 33 and spring retainers 34.

In operational mode the half nut pair 31a, 31b close about the screwed shaft of the screw operator 27 and thereby convert the rotary motion of the screw operator 27 to a linear motion as a result of the engagement of the threaded portions 34a, 34b of the half nuts 31a, 31b.

The syringe plunger driver can be quickly moved to a new position by disengaging the half nut pair from the screw operator by firstly urging the top portion of each member of the half nut pair inwardly towards the other so as to disengage the half nut pair from the screw operator 27 followed by a longitudinal manual shifting of the half nut pair assembly (together with the connected syringe portion 5) along the support rails 22.

The motor assembly 23 comprises a reduction gearbox 35, a permanent magnet DC motor 36 and an optical shaft encoder assembly 37. The optical shaft encoder 37 delivers pulses in direct proportion to the angular displacement of the shaft 28 of the DC motor 36. The number of pulses is hence also proportional to the linear displacement of the syringe plunger driver and hence also to the syringe plunger 5 when engaged in the slot 38.

The three items comprising the motor assembly 23 in the second preferred embodiment can be purchased from "Escap" of Switzerland as DC gearmotor part number M1616C11-205 combined with a type C optical encoder.

This unit provides a maximum static torque of 100 mNm and a maximum dynamic torque of 50 mNm for a gearbox reduction ratio of 729:1 at a terminal voltage of 6 volts.

One of the half nut pair 31b has a leading portion 39 of its thread 34b removed in order to prevent this member of the pair from automatically disengaging due to an observed frictional coupling between it and the screw operator whilst the screw operator is rotating and driving the syringe plunger driver under load.

Referring to FIG. 9 there is shown a form of "universal" coupling which allows latitude for misalignment between the shaft 28 and the screw assembly 27. This assembly of FIG. 9 can be used with either the first or second embodiments and replaces the boss 30 shown in FIG. 8. The universal coupling of FIG. 9 comprises a toothed washer 39 having a "D" shaped hole in its centre adapted to engage the gearbox shaft 28 about its portion having a flat thereon. The teeth of the washer 40 engage with recesses 41 in boss 42 which is clamped to the screw operator 27.

Figure 10A:
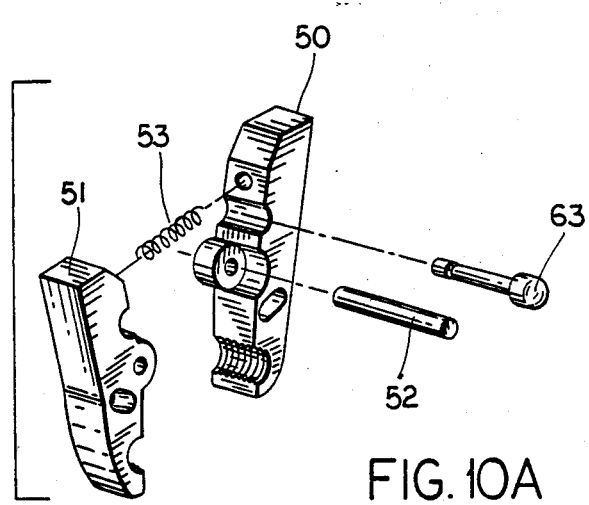
FIGS. 10A and 10B are exploded perspective and, partly in section, front views, respectively, of an alternative drive engagement/disengagement mechanism suitable for use with either the first or second embodiments.
Figure 10B:
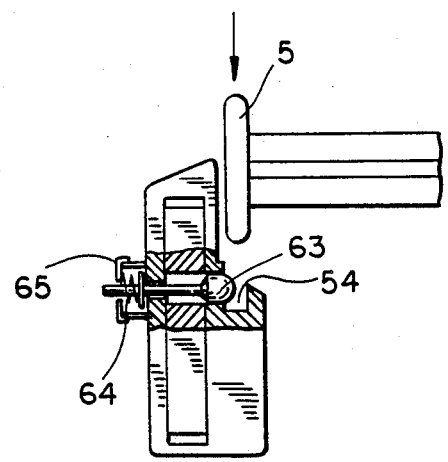

Referring to FIG. 10 there is shown an alternative way of preventing the half nut pair 31a, 31b from inadvertently, uncontrollably or accidentally being disengaged from the screw shaft 27. In this version (suitable for use with either the first or second embodiments of the invention) half nuts 50 and 51 (comparable to the half nuts 31b, 31a of FIG. 8) are joined by means of a pivot pin 52 passing through holes in the half nuts as shown. The half nut pair 50, 51 is maintained in its normal engaged position by compression spring 53 acting to push the top portions of the half nut pair away from each other about the axis 52. A locking pin 53 is supported within the syringe plunger driver as shown such that when the end of the plunger portion of syringe 5 is engaged in the slot portion 54 the pin 53 is pushed laterally so as to have at least a portion of its length located between the opposed end portions of the half nut pair 50, 51. The diameter of this portion of the pin 53 is large enough to prevent the end portions of the half nut pair 50, 51 from being able to collapse inwardly far enough to cause disengagement of the threaded portions of the half nut pair from the screw operator 27.

When the syringe 5 is removed the pin 53 is returned to the unlocked condition by means of spring 54 which is retained in a compressed condition by cap 55.

The above describes only some embodiments of the present invention and modifications obvious to those skilled in the art can be made without departing from the scope and spirit of the present invention.

For example the control philosophy can be used with any continuous drive system including AC motor drives.

Similarly, whilst a pulse encoder is the preferred form of obtaining volume delivery information, other systems, for example analogue systems, could be used together with analogue to digital conversion means.

In use, the drive mechanism and philosophy of the present invention can be used wherever accurately repeatable volumes of liquid are to be delivered over nominated periods of time. Such usage might include laboratory work with animals, food processing and areas of biotechnology.

Whilst the schematic diagrams of FIG. 4 and FIG. 6 shows a microprocessor embodiment the algorithm of the present invention could be implemented in pure hardware fashion.

We claim:

1. A method of controlling an infusion pump, said pump including a motor adapted to impart continuous rotary motion via an output shaft, said pump further including encoding means adapted to provide data indicative of rotational motion of said output shaft, said data being proportional to the angular displacement of said output shaft; said method comprising providing power to said motor only for a first period of time within a time window during which first data is produced from said encoding means; monitoring second data received from said encoding means during a second period of time immediately following said first period of time during said time window; comparing said first and second data with desired data corresponding to a predetermined volume feed rate of said infusion pump and, on the basis of said comparison, determining whether and for how long to energize said motor during subsequent window periods.

2. The method of claim 1 wherein said encoding means comprises a pulse encoder which produces output pulses proportional to angular displacement of said output shaft.

3. The method of claim 2 wherein said first data comprises pulses received from said encoder, the number of said pulses being proportional to the angular displacement of said output shaft during said first period of time during which and only during which power is provided to said motor.

4. The method of claim 3 wherein said second data comprises output pulses received from said encoding means during said second period of time, said second period of time being the time taken for said output shaft to come to a standstill following removal of power from said motor.

5. The method of claim 4 wherein said motor is a DC motor.

6. The method of claim 3 wherein said first data is compared with said second data so as to obtain an indication of pressure of liquid delivered by said pump.

7. The method of claim 1 or 5 wherein said window period lies in the range of 1-5 seconds.

8. The method of claim 7 wherein if said comparison indicates that less than a predetermined minimum amount of displacement of said output shaft is required for a subsequent window period then said motor is not energized during said subsequent window period.

9. The method of controlling an infusion pump as claimed in claim 1 wherein the step of comparing said first and second data with desired data is additionally used to determine pressure of liquid delivered by said infusion pump.

10. An infusion pump including a motor adapted to impart continuous rotary motion via an output shaft, said pump further including encoding means adapted to provide data indicative of rotational motion of said output shaft, said data being proportional to the angular displacement of said output shaft; said pump further including means to provide power to said motor only for a first period of time within a time window during which first data is produced from said encoding means; comparison means for comparing said first data and second data received from said encoding means during a second period of time immediately following said first period of time during said time window with desired data corresponding to a predetermined volume feed rate of said infusion pump; said comparison means determining whether and for how lng to energize said motor during subsequent window periods on the basis of the comparison.

11. The pump of claim 10 wherein said encoding means comprises a pulse encoder which produces output pulses proportional to angular displacement of said output shaft.

12. The pump of claim 11 wherein said first data comprises pulses received from said encoder, the number of said pulses being proportional to the angular displacement of said output shaft during said first period of time during which, and only during which, power is provided to said motor.

13. The pump of claim 12 wherein said second data comprises output pulses received from said encoding means during said second period of time, said second period of time being the time taken for said output shaft to come to a standstill following removal of power from said motor.

14. The pump of claim 10 or claim 13 wherein said motor is a DC motor.

15. The pump of claim 14 wherein said time window lies in the range 1-5 seconds.

16. An infusion pump as claimed in either claim 10 or claim 12 wherein said comparison means compares said first data and said second data to provide a determination of pressure exerted by said pump on liquid pumped by said pump.

17. A method of controlling an infusion pump, said pump including a DC motor connected by its output shaft to a reduction gearbox and thence to a rotary to linear motion converter, said converter imparting linear thrust to a syringe piston; said shaft of said DC motor also driving encoding means, said encoding means providing output pulses in proportion to angular displacement of said shaft; said method comprising: providing power to said DC motor only for a first period of time within a time window during which a first series of output pulses is produced from said encoding means; monitoring said output pulses (as said shaft of said DC motor returns to a stationary state) during a second period of time during said time window; comparing said pulses with a desired number of pulses corresponding to a predetermined volume feed rate and, on the basis of said comparison, determining whether and for how long to energize said DC motor during subsequent window periods.

18. An infusion pump, said pump including a DC motor connected by its upward shaft to a reduction gearbox and thence to a rotary to linear motion converter, said converter imparting linear thrust to a syringe piston; said shaft of said DC motor also driving encoding means, said encoding means providing output pulses in proportion to angular displacement of said shaft; said pump including control means to supply power to said DC motor only for a first period of time within a time window during which a first series of output pulses is produced from said encoding means; said control means monitoring said output pulses (as said shaft of said DC motor returns to a stationary state) during a second period of time during said time window; said control means comparing said pulses received during said first and said second periods and comparing said pulses with a desired number of output pulses corresponding to a predetermined volume feed rate and, on the basis of said comparison, determining whether and for how long to energize said DC motor during subsequent window periods.

19. The pump of claim 18 wherein the acceleration of said output shaft is approximately constant during said first period of time and deceleration of said output shaft is approximately constant during said second period of time and said first period of time is set to expire when half said desired number of pulses have been received by said control means.

20. The pump of claim 19 wherein said first period of time and said second period of time are approximately equal.

21. The pump of claim 20 wherein the total length of said first period of time and said second period of time does not exceed 1 second.

22. The pump of claim 21 wherein said time window is approximately 4 seconds, said reduction gearbox has a reduction ratio of approximately 700:1, said syringe piston has an inside diameter of approximately 15 mm plus/minus 0.5 mm and said delivery rate does not exceed 5 ml/hr.

23. The pump of claim 21 wherein said time window is approximately 2 seconds, said reduction gearbox has a reduction ratio of approximately 700:1, said syringe piston has an inside diameter of approximately 15 mm plus/minus 0.5 mm and said delivery rate does not exceed 10 ml/hr.

24. The pump of claim 18 wherin thrust is imparted to said syringe by means of two opposedly mounted half nuts releasably clamped in threaded engagement with a longitudinal, threaded screw operator.

25. The pump of claim 24 wherin a leading sector of a threaded portion of one of said two half nuts has the thread removed so as to prevent inadvertent frictional disengagement when under load.

* * * * *